(12) United States Patent
Bension

(10) Patent No.: US 7,163,658 B2
(45) Date of Patent: Jan. 16, 2007

(54) RAPID SEQUENCING OF POLYMERS

(76) Inventor: Rouvain Bension, 310 Summit Ave., Brighton, MA (US) 02135-7504

( * ) Notice: Subject to any disclaimer, the term of this patent is extended or adjusted under 35 U.S.C. 154(b) by 577 days.

(21) Appl. No.: 10/421,343

(22) Filed: Apr. 23, 2003

(65) Prior Publication Data

US 2004/0214177 A1   Oct. 28, 2004

(51) Int. Cl.
*G01N 15/06* (2006.01)
*G01N 33/00* (2006.01)
*G01N 33/48* (2006.01)
*C21Q 1/68* (2006.01)

(52) U.S. Cl. .............................. 422/68.1; 422/50; 435/6
(58) Field of Classification Search .................... 435/6; 422/50, 68.1
See application file for complete search history.

(56) References Cited

U.S. PATENT DOCUMENTS

2002/0086318 A1   7/2002   Manalis et al.

FOREIGN PATENT DOCUMENTS

DE   44 10 655 A1   9/1995

OTHER PUBLICATIONS

Deamer, David W. & Branton, Daniel, *Characterization of Nucleic Acids by Nanopore Analysis*, pp. 817-825, Accounts of Chemical Research, vol. 35, No. 10, 2002.

*Primary Examiner*—Jezia Riley
(74) *Attorney, Agent, or Firm*—Robert G. Rosenthal; Robert L. Goldberg

(57) ABSTRACT

A method and device for sequencing at least a fragment of a linear polymer. The device comprises a well for placement of a rotaxane comprising the combination of a cyclic molecule and a linear polymer threaded through said cyclic molecule; a probe having the ability to move the linear polymer relative to the cyclic molecule while producing a signal resulting from the interaction of the cyclic molecule and a unit attached to the polymer; and means for reading said signal. The process comprises formation of the rotaxane, attachment of the probe, movement of the cyclic molecule relative to the linear polymer and the reading of signals. The device and method are especially useful for the sequencing of DNA.

20 Claims, No Drawings

RAPID SEQUENCING OF POLYMERS

Work described herein has been supported, in part, by the Naval Research Laboratory under contract Number N00173-01-2011. The United States Government may therefore have certain rights in the invention.

BACKGROUND OF THE INVENTION

1. Introduction

This invention relates to the rapid sequencing of long linear polymers. More particularly, the invention relates to the formation of a rotaxane comprising the polymer to be sequenced and a judiciously selected cyclic molecule which is slid along the polymer by a probe that detects the change in signal as the cycle passes from one monomer or unit of the polymer to the next. In a preferred embodiment the invention relates to the sequencing of DNA using a scanning probe microscope.

2. Description of the Prior Art

Since the sequence of monomers in a polymer chain determines its properties, such information is of great interest to the chemical industry. This interest is nowhere more intense than in the sequence of deoxyribonucleic acid (DNA), the polymer that determines the physiological properties and function of virtually every living organism. Just to obtain a working draft of the human genome sequence, for example, the United States Government spent $300 million dollars from 1990 to date, with an additional $200 million estimated to complete the task by the end of 2003. This work is expected to result in improvements in forensic analysis; diagnosis of genetic disease or predisposition thereto; bio-terrorism and biowarfare countermeasures; pharmaceutical research and development, including a cure for cancer; and genetic engineering for agricultural, chemical, waste-remediation, and other products.

Current sequencing methods are very slow. As mentioned above, the human genome sequence has required thirteen years to complete. Even using accelerated technology and relying on accrued databases, Celera Genomics Inc., Rockville, Md., spent nine months on a similar program. In addition, existing sequencing methods suffer from a frequency of inaccuracies that make tedious error-checking necessary.

The most widely used DNA sequencing technology is described by H. G. Griffin, A. M. Griffin, eds., *DNA Sequencing Protocols*, in *Methods Mol. Biol.* (Humana Press, Totowa, N.J.), vol. 23, 1993. It is based on that reported by Sanger et al, *Proc. Natl. Acat. Sci USA,* 1977, 74, 5463 and augmented by the polymerase chain reaction (PCR), reviewed by I. S. Bevan, R. Rapley, M. R. Walker, *PCR Methods Appl.,* 1992, 1, 222. Each of the three publications above is incorporated herein by reference.

The method described in the above reference employs four steps: first, the DNA is enzymatically cleaved into fragments of manageable size, about 500 bases long; second, each fragment is replicated via PCR, from a mixture of normal nucleotides and some bearing 3'-dideoxy sugars. When one of the latter is incorporated in the replication, it terminates the fragment, since the 3'-OH group from which the chain would be extended is absent. The fraction of dideoxy nucleotides is adjusted to ensure that their incorporation will result statistically in a population of chains that includes all lengths from 2 to 500.

Third, the populations are chromatographed using a gel that separates them by chain length; thus each chain passing through contains one more nucleotide than that eluting before it. And fourth, each of the terminating nucleotides having been labeled specifically with one of four different dyes, the sequence of the ~500-base fragment from which all the chains were made can be read by identifying the dye fluorescing in each fraction.

The Maxam-Gilbert method is similar, labeling the 5' end of the 500-base fragment, and then cleaving chemically rather than enzymatically. In addition, each of the chemical agents cleaves specifically at one of the four nucleotides. The four mixtures are then separated in four lanes on a gel plate by length. After labeling the plate abcissa with A, C, G, and T, and the ordinate with all of the possible chain lengths, the sequence can be read.

Each of these methods requires steps of replication, cleavage, labeling, and reading, a tedious process prone to errors. To address these problems, machines have been developed, chiefly by Applied Biosystems, presently a division of Applera Corporation, that not only carry out the process automatically, but can sequence many samples simultaneously.

The deficiencies in the current technology have been addressed by other methods. A group at Affymetrix Inc., Santa Clara, Calif. has developed a chip sequencer, disclosed by Fodor et al in PCT Int. Appl. WO 95 00,530. All possible combinations of an octanucleotide are deposited photolithographically onto a silicon chip, in the first step divided into, e.g., quadrants, each covered by one of the four nucleotides containing protective groups. The area is divided into eight sections and the protective groups are selectively photolyzed and reacted with another layer of nucleotides, these steps being repeated until an entire octanucleotide monolayer has been deposited in an array of $4^8$ or 65,536 bases. To detect which sequence is interacting with the target octanucleotide, the chip bases or the target molecule are modified with a fluorescent dye. Since the target molecule may not bind to the chip with 100% specificity, more than spot will fluoresce; the brightest one is considered to be the matching sequence. In order to increase the number of nucleotides per test spot—currently up to 25—an algorithm is used to eliminate those sequences least likely to be a match. Array technology has been reviewed by Li et al, *Microcirculation,* 2002, 9, 13, incorporated herein by reference.

A mass spectrometric (MS) sequencing method based on Sanger sequencing has been disclosed by Fu et al in U.S. Pat. No. 6,436,635; MS sequencing has been reviewed by Uber and Oberacher, *Mass Spectrometry Reviews* 2001, 2002, 20, 310, incorporated herein by reference.

Pyrosquencing proceeds in ofur steps: (1) synthesis of the DNA strand complementary to the unknown; (2) release of one pyrophosphate molecule (PPi) per nucleotide incorporated; (3) conversion of PPi by ATP sulfurylase to adenosine triphosphate (ATP); ATP-powered oxidation of luciferin by luciferase, resulting in light emission. Only the matching base will cause the system to light, allowing determination fo the sequence. This technique has been reviewed by Fakhrai-Rad et al, *Human Mutation,* 2002, 19, 479, incorporated herein by reference.

A single-molecule procedure developed by Keller at Los Alamos National Laboratory is discussed by Ambrose et al, *Ber. Bunsen-Ges. Phys. Chem.,* 1993, 97, 1535, incorporated herein by reference. A DNA molecule is replicated from a pool of nucleotides, all of which are fluorescently labeled and suspended in a flowing stream. The nucleotides are cleaved sequentially with an exonuclease, and the individual fluorescently labeled bases identified as they are carried downstream past a laser-induced fluorescence detector.

However, the replicating enzyme is often confused by a labeled base, resulting in incorporation of a base different from that in the DNA to be sequenced, and leading to an error. Since in a real analysis the original sequence would be unknown, no basis for comparison would exist, and the error would not be detected. Also, it is difficult to control the exonuclease rate or processivity, especially critical in a flowing stream, where the enzyme will be washed away if it falls off.

A number of approaches based on scanning probe microscopy have been published. Atomic force microscopy (AFM) has been disclosed by Bensimon et al, in PCT Int. Appl. WO 94 23,065 to measure the energy required to separate each pair of bases in a double-stranded (ds) DNA molecule or the energy obtained from pairing a single-stranded (ss) DNA with a standard. The identity of the base, and hence the sequence, can be obtained from the energy value. It is clear, however, that this value must change as the point of separation recedes from the AFM tip, or that the tip must be repositioned over each base pair to be separated. Moreover, the energy required to break the hydrogen bonds between complementary bases is low enough to disapper into ambient thermal noise.

Sequencing by chemical force microscopy (CFM), i.e. AFM with a chemically modified tip that interacts differently with each base, has been discussed by G. U. Lee et al, *Isr. J. Chem.*, 1996, 36, 81, incorporated herein by reference. A substrate with pathways to align labeled DNA molecules for sequencing by scanning tunneling microscopy (STM) has also been disclosed, by Sargent et al in PCT Int. Appl. WO 96 24,689.

Cherkasky has disclosed a method in German Patent No. 19,937,512 for purifying chromosomal DNA, immobilizing it on a long glass plate, and stretching it linearly.

Methods involving the threading of DNA through pores have been reviewed by Deamer and Branton, *Acc. Chem. Res.*, 2002, 35, 817, incorporated herein by reference. A nanopore is formed by inserting α-hemolysin into a lipid membrane, which is plated on both surfaces. The membrane is immersed in an electrolyte solution and the current measured. When a single-stranded oligonucleotide is shot through the pore by an electric field, it excludes electrolyte from the pore and interrupts the current. When the junction in a block oligonucleotide passes through the portal, i.e., when the base changes, a momentary peak appears signaling the event.

Chan discloses the use of a molecular motor, a particular class of enzyme such as a DNA polymerase, in U.S. Pat. No. 6,210,896. The molecular motor, labeled with a fluorescing function, either moves along, or causes to pass through itself, a DNA labeled with other fluorescing functions. Electromagnetic radiation is continuously supplied, so that when the molecular motor passes over one of the labels, the energy transfer between the two fluorescing functions can be detected. The molecular motor is held by electrostatic force in channels fabricated in the apparatus near the detector.

Although not acknowledged in the specification, the enzyme possesses a pore in the form of the so-called "sliding clamp." Certain DNA polymerases "achieve high processivity by the attachment of their catalytic subunits to a 'sliding DNA clamp' . . . which are bound to DNA by virtue of their topology and have to be assembled on DNA by other proteins . . . " (Krishna et al; *J. Mol. Biol.*, 1994, 241, 265, incorporated herein by reference). The sliding clamp, which prevents the polymerase from falling off the DNA strand, has been reviewed by Jeruzalmi et al, *Current Opinion in Structural Biology*, 2002, 12, 217, incorporated herein by reference.

Allen has disclosed a method incorporating both a pore and AFM in U.S. Pat. No. 6,280,939. However, although the patent describes the need for a label as a disadvantage of previous techniques, it requires "flagging" the various nucleotides by introducing base-dependent conditions, such as time of incorporation.

Manalis has disclosed a sequencing method in U.S. patent application Ser. No. 2002 86,428 also using a polymerase, but with a so-called "single electron transistor" that measures the electric charge configuration around the polymerase, which is said to change depending upon the base passing through the polymerase.

SUMMARY OF THE INVENTION

In contrast to present electrophoresis-based or array-chip methods requiring the duplication, labeling, separation, and integration of many fragments, the method disclosed herein reads directly from a single intact DNA molecule, avoiding stutters and replication errors of polymerases over repetitive sequences from secondary loop structures. The present invention passes only the "hole" and not a membrane over the DNA, while the hole is attached to a reading head; or pulls the DNA through a pore, fashioned in a material or device of choice, in which a reading head is integrated. Thus, although the description which follows is directed primarily to one where the polymer is fixed and a bead moves, it encompasses any system in which the bead and the polymer are moved relative to each other. No reactions are required at the sequencing step; the method detects intrinsic properties of each nucleotide, such as the mechanical force required to drag the cyclic molecule over the nucleotide, or the oxidation-reduction (redox) or other electrical properties of the nucleotide base.

It therefore permits easy resequencing of areas of questioned reads; allows reads of larger lengths of DNA; and allow greater read rates. Although DNA is presented herein as the preferred embodiment, the invention applies equally well to the sequencing of any polymer, including RNA, proteins and plastics.

DESCRIPTION OF THE PREFERRED EMBODIMENTS

As described in greater detail below, the invention utilizes rotaxanes, in their simplest forms systems consisting of two molecules: a "thread," or polymeric molecule, and a "bead" or cyclic molecule which is strung on the thread. They have been reviewed in J. Becher, K. Schaumburg, eds., *Molecular Engineering for Advance Materials*, (Kluwer, Boston) 1995, incorporated herein by reference. In stable systems the ends of the polymeric molecule are functionalized after threading with "stoppers," substituents too large to allow the bead to fall off. Rotaxanes are therefore held together mechanically but not chemically. This approach is biomimetic, because the bead is an analog of the sliding clamp, described above.

The class of compounds that has received the most attention as a bead is the cyclodextrins [hereafter CD(s)], reviewed by J. Szejtli, T. Osa, eds., *Cyclodextrins, vol. 3* in J. L. Atwood, J. E. D. Davies, D. D. MacNicol, F. Vogtle, eds., *Comprehensive Supramolecular Chemistry* (Pergamon, New York) 1996 (hereinafter CSC); and their rotaxanes have been reviewed by Harada; *Carbohydr. Polym.*, 1997, 34, 183 and Nepogodiev and Fraser; *Chem. Rev.*, 1998, 98, 1959.

These cyclic oligomers of glucose linked at the α-1,4 positions are available commercially as hexa-, hepta-, and octamers, (α-, β- and γ-CD, respectively) from Cerestar, Wacker, and other suppliers. Sizes up to heptadecamers are accessible in the laboratory, using methods published in Fujiwara et al, *Chemistry Letters,* 1990, 739; Endo et al, *Carbohydrate Research,* 1995, 269, 369; Ueda et al, *Journal of Inclusion Phenomena and Molecular Recognition in Chemistry,* 1996, 25, 17; and Endo et al, *Chemical and Pharmaceutical Bulletin,* 1997, 45, 1856. A synthesis of CD analogs based on L-rhamnose and D-mannose with even numbers of sugars from 6 to 14 has been reported by Nepogodiev et al, *Journal of Inclusion Phenomena and Molecular Recognition in Chemistry,* 1996, 25, 47, the eight foregoing publications incorporated herein by reference. The three commercially available CDs are tapered cylinders with interior diameters of 4.7–5.3, 6.0–6.5, and 7.5–8.3 Å, respectively, capable of forming inclusion complexes; i.e., there is a driving force for certain "guest" molecules to enter and remain in the cavity of the CD.

When the guest is a polymer, the resulting complex is a rotaxane. Only certain polymers form rotaxanes with each size of CD; in these cases, it is sufficient merely to mix the polymer and CD to form the rotaxane; i.e., it will self-assemble. Some polymers that form rotaxanes with γ-CD are poly(propylene glycol) (PPG), poly(methylvinylether) (PMVE), polytetrahydrofuran, and polyisobutylene (PIB); with β-CD, PPG; and with α-CD, polyethylene glycol (PEG). CD rotaxanes have been reviewed by Harada in *Advances in Polymer Science,* 1997, 133, 141, and in *Acta Polymerica,* 1998, 49, 3, both incorporated herein by reference; the latter review covers other beads, also. CD complexes with DNA are discussed by Redenti et al, *Advanced Drug Delivery Reviews,* 2001, 53, 235, incorporated herein by reference.

Calixarenes, which are cyclic tetra-, hexa-, and octamers of resorcinol and its derivatives, are the subject of an entire book by Gutsche, *Calixarenes* (Royal Society of Chemistry, Cambridge, UK) 1989, and comprehensive reviews by Boehmer, *Angewandte Chemie International Edition in English,* 1995, 34, 713, and in F. Vögtle, ed., *Molecular Recognition: Receptors for Molecular Guests,* vol. 2 in CSC cited above. Crown ethers, cyclic oligomers of ethylene glycol and/or resorcinol, and their analogs are reviewed in G. W. Gokel, ed., *Molecular Recognition: Receptors for Cationic Guests,* vol. 1 in CSC cited above, and their rotaxanes in Harada; *Acta Polymerica,* 1998, 49, 3, cited above. Cucurbiturils, cyclic co-oligomers of glycoluril (acetyleneurea) and formaldehyde, have also been reviewed in Gokel, CSC, by W. L. Mock, p. 477, and their rotaxanes by Kim, K.; *Chemical Society Reviews,* 2002, 31, 96. The preceding seven reviews are incorporated herein by reference.

Schwertner in German patent no. 4,410,655, incorporated herein by reference, describes such components of the present invention as rotaxanes employing cyclodextrin beads, tethering chains for DNA, electric fields for moving the bead, and fluorescence detectors, but no details of how to use them, nor examples, nor references to methods it characterizes as well-known.

Circular DNA has been found to form triplexes with linear dsDNA by Ryan and Kool; *Chem. Biol.,* 1998, 5, 59, incorporated herein by reference, who detected the formation of a rotaxane, inferring that the circular DNA self-threads onto the linear dsDNA and slides along until it reaches a binding site. The article is featured on the cover of the issue in which it appears with an illustration of the general kind of rotaxane described in this invention, and the authors compare it with the protein sliding clamp but apparently consider it not useful for sequencing; it " . . . might be more valuable as a new strategy for DNA binding by synthetic ligands than as a model of protein sliding clamps."

The β-barrels are also suitable for the invention, consisting of four phenyl octamers (octiphenylenes), each with oligopeptide sidearms on alternating phenyl groups that interleave with those on the neighboring octiphenylene. Examples are described by Baumeister and Matile, *Chem. Commun.,* 2000, 913, incorporated herein by reference.

Also contemplated herein are metallic nanorings, which could be formed by plating circular DNA. Individual molecules of linear DNA have been plated by both electrolytic and electroless methods, reported by Braun et al, *Nature,* 1998, 391, 775, and Richter et al, *Advanced Materials,* 2000, 12, 507, respectively, both incorporated herein by reference.

As mentioned above, in a preferred embodiment the bead is moved by an AFM or STM tip at a speed that will dramatically shorten the analysis time presently required for sequencing. A measure of bead speed can be derived from a rotaxane system reported by Lane et al., *J. Am. Chem. Soc.,* 1997, 119, 11092, incorporated herein by reference, with a thread containing a sulfur atom disubstituted with a triethylene oxide ester of a dipeptide. The dipeptide ends were capped with biphenyl groups to retain the cyclic tetrapeptide bead. The shuttling rate of the bead between the two dipeptide stations on the thread is 62,000 cycles per second. The distance between the two stations is 18 atoms, or a straight line of about 22 Å vs. 7.1 Å for the completely stretched internucleotide distance. The rate of travel is then 2 lengths/cycle×3 nucleotides/length×62,000 cycles/second=372,000 nucleotides per second, or 351 seconds (6 minutes)/$10^8$ nucleotides, the approximate length of the average human chromosome.

Using this method, therefore, if rotaxane-based sequencing processes were set up in parallel for the 23 chromosomes, the time required to sequence the human genome could be reduced to less than six minutes.

The process of the invention requires up to five steps: terminal modification of the DNA molecule to be sequenced; threading of the bead onto the DNA; tethering or immobilizing the DNA via the modified terminus; stretching the DNA; moving the bead and reading the signal; and translating the seqence of signals into the sequence of bases.

Tethering to a surface allows the bead to be slid all the way from one end to the other without catching and dragging the DNA. A spacer may be added as part of the terminal modifier to allow the bead clearance at either end of the DNA, like a leader or trailer on a magnetic recording tape. The other terminus can be modified to facilitate stretching the molecule. These reactions can be carried out following the classical methods used for natural DNA, described in Chu, B. C. F., and Orgel, L. E., "Postsynthesis Functionalization of Oligonucleotides," in Walker, J. M., ed.; Agrawal, S., ed.; *Methods in Molecular Biology, Vol. 26: Protocols for Oligonucleotide Conjugates* (Humana Press, Totowa, N.J.) 1994, Ch. 5., both incorporated herein by reference.

The 3' end of the DNA can be thiolated and covalently bound to the surface. For example, Chrisey et al; *Nucleic Acids Res.,* 1996, 24, 3031, incorporated herein by reference, have reported thiolation and covalent binding of an oligonucleotide to a self-assembling monolayer (SAM)

The 5' terminal can be phosphorylated using adenosine triphosphate and polynucleotide kinase. Thiolation can be accomplished by reaction of the 5' phosphate with imidazole and carbodiimide (CDI), followed by reaction of the resulting imidazolide with cystamine. If the disulfide fails to react to form a covalent sulfur bond with the intended target, the thiol can be generated by reaction of the cystamine S—S bond with dithiothreitol [DTT, $HSCH_2CH(OH)CH(OH)CH_2SH$]. The reaction can now be repeated on the 3' end using instead of cystamine, an alkane diamine $H_2N—(CH_2)_n—NH_2$ or PPO diamine, $H_2N—(CH_2CH(CH_3)O)_n13\ NH_2$, available commercially. Alternatively, the 5' end can be amine-functionalized and deposited onto a SAM-modified surface bearing exposed alkyl halides.

As another option, an oligonucleotide with desirable terminal modifications can be synthesized and then enzymatically ligated to the sample DNA. Bamdad has reported in *Biophys. J.,* 1998, 75, 1997, and Bamdad et al have disclosed in U.S. Pat. No. 6,472,148, both incorporated herein by reference, the use of a SAM for this purpose. The SAM monomer consists of four segments: a thiol group, methylene chain, triethylene glycol, and DNA decamer. The decamer is hybridized with a dsDNA containing a complementary 10-mer overhang, and ligated to the dsDNA. The system is then heated to remove the overhanging strand, leaving ssDNA tethered via triethylene glycol (a polyoxyethylene [PEO] oligomer) to a surface. Substitution of the PEO by a PPO would allow self-threading of either a β- or γ-CD bead followed by deposition of the complex on the surface.

The approaches just described are meant to be representative and not limiting; other tethering chemistry, for example has been spurred by the chip-sequencing technology described previously herein.

Stretching the DNA molecule sufficiently will straighten out kinks that would otherwise impede bead movement. If it is stretched both out and upward, then the bead will not have to overcome DNA-surface interactions, and it will be possible to slide the bead in either direction. Methods of stretching DNA, chiefly with magnetic particles or optical tweezers, have been reviewed by Frank-Kamenetskii, M. D.; *Molecular Biology (Translation of Molekulyarnaya Biologiya)* 2002, 36, 232, incorporated herein by reference.

A preferred embodiment of the invention is the sequencing of ssDNA to avoid any confusion between bases on main and complementary sequences. However, the self-association problem of ssDNA must be overcome. Allemand et al; *Biophys. J.,* 1997, 73, 2064, incorporated herein by reference, report that dsDNA can bind to a variety of substrates by its sticky ends, i.e. one of the strands which continues past the end of the other. Binding is dependent on the pH. Moreover, once bound, a receding meniscus can stretch the DNA like a hair being combed straight.

Electrostatic stretching may also be used. DNA can be tethered by one end to a surface capable of accepting a high electrical potential. The voltage can then be raised to the break-down value. Zimmerman and Cox cited above reported an electric field as low as 5 V/cm to stretch dsDNA tethered at one end, Washizu et al; *IEEE Trans. Ind. Appl.,* 1995, 31, 447, reported similar stretching, and Chan employs the method in U.S. Pat. No. 6,210,896 cited above.

Finally, the free end can be tethered to a magnetic particle and stretched by a magnet, as reported by Smith, S. B.; Finzi, L.; Bustamente, C.; Science, 1992, 258, 1122, incorporated herein by reference. Puntes et al; *Topics in Catalysis,* 2002, 19, 145 report preparation of magnetic cobalt nanoparticles. Dyal et al; *Journal of the American Chemical Society,* 2003, 125, 1684 report covalent attachment of *Candida rugosa* lipase covalently immobilized via an alkyl chain spacer on γ-$Fe_2O_3$ magnetic nanoparticles.

As mentioned above, self-threading may be facilitated by using a polypropylene oxide (PPO) oligomer to modify the 5' end.

Once the DNA is threaded and stretched, the CD is picked up by the probe and slid along the DNA backbone. Indeed, Komiyama et al; *Polym. Mater. Sci. Eng.,* 1999, 80, incorporated herein by reference, have reported pushing an α-CD bead along a polyethylene glycol thread by STM, even around bends. The present invention requires the probe to be attached so that it will not be lost during the reading of the sequence. The preferred method of attachement is covalent. For example, a cyclodextrin bead can be thioalkylated for attachement to a gold-coated microscope tip. Such alkylthiolations have been reported by Henke et al, *Anal. Chem.,* 1996, 68, 3158, incorporated herein by reference.

The preferred method of probe movement and signal detection is scanning probe microscopy. Analysis at the nanometer level by this technique is well known, reviewed comprehensively, for example, by Wiesendanger, *Scanning Probe Microscopy and Spectroscopy: Methods and Applications* (Cambridge University Press) 1994. Single molecule studies using local probes have been reviewed by Gimzewski and Joachim, Science, 1999, 283, 1683. As an example, Leatherman et al; *J. Phys. Chem. B,* 1999, 103, 4006, were able to image single carotenoid molecules in a docosanethiol (n-$C_{22}H_{45}SH$) SAM on gold by using conducting AFM to oxidize or reduce them.

The invention contemplates other methods of detection, for example adaptations of the traditional spectrophotometric methods relying on the absorption or emission of electromagnetic radiation by the sample of interest. The first application of magnetic resonance force microscopy (MRFM) was a relatively coarse image published by Zuger and Rugar, *Applied Physics Letters,* 1993, 63, 2496, but a white paper to the Defense Advanced Research Projects Agency by the University of Washington available on line at http://courses.washington.edu/goodall/MRFM_technical_summaries/M OSAIC_UW_2002.pdf predicts the development of resolution sufficient for the present invention by 2006. The five citations above are incorporated herein by reference. While other techniques such as infra-red, ultraviolet-visible, and the like have not yet received similar attention, they are anticipated to have equally useful applicability.

The present invention contemplates the processes described above, e.g. redox identification, while moving the bead along the thread to produce an electrical signal characteristic of each nucleotide base. For STM, instead of constant current from the tip to the substrate the instrument can be operated as a potentiostat. The current will change depending upon the electron density around the base. The sequence of electrical current readings will be the raw data from which the sequence of bases can be deduced. In another embodiment, the repulsive (or attractive) forces deflecting the AFM cantilever can be converted to a voltage, the magnitude of which again will depend on the base. In each case, the signal will include values as the tip approaches the base, passes over it, and leaves.

The probe may be modified in any way suitable to the practice of the invention. For example, while the apex radius of most currently available AFM tips is about 15 nm, a carbon nanotube may be affixed to the tip, functioning as a much finer extension, capable of concomitantly improved resolution, as described by Gotoh et al, *Japanese Journal of Applied Physics, Part* 1, 2002, 41, 2578, incorporated herein by reference.

The bead may also be modified, not only for attachment of the probe as described above, but also to increase the unique interaction with the polymer unit. For example, a CD might be functionalized with one or more nucleotide bases to produce a unique drag on-and mechanical deflection of the cantilever over one or more bases.

Although nucleic acids and especially DNA are the focus herein, the process can also be applied to other polymers, such as proteins with 20 comonomers, or polymers for the plastics industry, with usually only 2 or 3. Indeed, β-CD complexes of polypeptides terminally modified with PEG/PPG block oligomers for the purposes of precipitation and purification have been disclosed in Russian patent no. 2,063,985. Sebille et al claim in PCT international appl. 02/100801 the reversible immobilization of biological molecules that have been terminally modified with PEG by complexation with surface-bound cyclodextrins or their polymers. A drug delivery complex of DNA electrostatically bound to a poly (propyleneimine) dendrimer, in turn complexed non-covalently with cucurbituril is reported by Lim et al, *Bioconjugate Chemistry*, 2002, 13, 1181. The use of these complexes for sequencing was apparently not contemplated in any of the above three publications.

Ultimately, the process disclosed herein is suitable for use in an instrument having wide utility. The preparation of that instrument employs microelectromechanical (MEMS) technology for fabrication of micro- or nanoseparators and reactors and devices. A DNA lab-on-a-chip "complete with a liquid metering and mixing system, reaction chamber, separation system, and fluorescence detector" which has the ability "to shuttle discrete 120-nL drops of solution and reagents between components of the chip" was described by Burns et al, *Science*, 1998, 282, 484, incorporated herein by reference.

All of the principal steps required to modify dsDNA to be sequenced are described by either Chu or Agrawal, cited above. The target DNA could be introduced in solution via pipet to the first well of such a system containing a decamer, which would be ligated to the 5' end using DNA ligase. The product solution would be transferred and purified electrophoretically via a microchannel to the next well. The 3' end can be phosphorylated using cytosine triphosphate (CTP), terminal transferase (ttase), cacodylate buffer, and $CoCl_2$, and the product again transferred and purified electrophoretically via a microchannel to the third well. The nucleotide can be removed, leaving only the phosphorylated end, using di-n-propylmalonic acid (DNPA) and $NaIO_4$, and the product purified by pumping through a microchannel containing a high-performance liquid chromatography (HPLC) packing into the fourth well. The phosphorus can be replaced by sulfur using 1-ethyl-3,3-dimethylaminopropyl-carbodiimide (CDI) followed by imidazole and then cystamine, again followed by HPLC purification. Reaction with magnetic iron nano- or microparticles can be carried out by mixing in the fifth well, an adaptation of the procedure of Dyal et al cited above.

An area on the side of this last well will have been precoated with the SAM reported by Bamdad, cited above, but optionally containing a PPG instead of a PEG segment and pre-threaded with the CD, as described above. The target DNA will be complexed via the decamer with the decamer of the SAM, and the non-complementary strand ligated to the SAM decamer. The well will be heated to denature the DNA and the non-tethered strands pumped out of the well via a microchannel.

This well will also contain one or more electromagnets designed to produce a field pulling the magnetic particle, e.g., toward an area of the wall opposite the tether and stretch the DNA. The well will have a diameter great enough to accommodate the entire stretched length of the target DNA. Such electromagnetic stretching has been described by Haber and Wirtz, *Review of Scientific Instrumentation*, 2000, 71, 4561, incorporated herein by reference.

The chip will be placed in a scanning probe microscope, for example an AFM. The AFM tip will be lowered to the CD until the attractive force is great enough to seize it. The CD will then be moved along the DNA in a direction from the tether toward the magnetic particle. The signals deteced by AFM from each of the nucleotides will be recorded and translated into a code by comparison with previously analyzed standards.

The raw data may be used in any of a variety of ways. For example, it would be possible to sequence healthy and cancerous cells from the same organ, determine that part of the cancerous sequence differing from the healthy one, and design a therapeutic agent targeting the unique cancerous sequence. Such a strategy could be used against any biological antagonist. Forensic identification is another use; indeed the wide publicity given the DNA evidence presented in *People of California* v. *Simpson* was one of the inspirations for this invention. This invention also represents the read cycle of a biomolecular computer, described by Adleman, *Science*, 1994, 266, 1021, incorporated herein by reference.

The following examples describe procedures for synthesis, threading, microscopy, data collection, and data analysis enabling the practice of the invention. All chemicals were purchased from Sigma-Aldrich or MB (MB) and used as received unless otherwise noted.

$PPG_{400}$-maleimide adduct. Poly(propylene glycol) bis(2-aminopropylether) ($PPG_{400}$, $\overline{M}_n$~400; 40 mg, 100 µmol) was dissolved in dimethylformamide (DMF, 1 mL) to yield a 100 mM solution. Then succinimidyl 4-(N-maleimidomethyl) cyclohexane-1-carboxylate (SMCC, MB, Boulder, Colo.; MW 334, 40.0 mg, 120 µmol) and triethylamine (25 µL, 120 µmol) were added and mixed for 1 hr, giving 100 mM of the $PPG_{400}$-maleimide product. Mass analysis of this solution by MALDI-TOF revealed a composition of >80% mono $PPG_{400}$-mal, ~10% unreacted $PPG_{400}$ and ~10% bis-maleimide $PPG_{400}$). Ethanol (EtOH, 2 mL) was then added, giving a final concentration of 33 mM $PPG_{400}$-maleimide adduct.

DNA-bis ($PPG_{400}$). A 50-nucleotide DNA oligomer with a $(ACTG)_{12}AC$ sequence and both 5' and 3'-thiolation (ATGC Genetics LLC, Phoenix, AZ; MW 15370; 50 nmol) was dissolved in tris(2-carboxyethyl)phosphine buffer (TCEP, MB, 40 µL, 10 mM; $NaH_2PO_4$, 5 mM; adjusted to pH 7.0 with NaOH) and mixed for 15 min. Then 20 µL of this solution (1.25 mM, 25 nmol, 50 neq) was combined with an excess of $PPG_{400}$-maleimide adduct (30 µL, ~1 µmol) to avoid mono- or unreacted oligomers in the product solution and mixed for 2 hr. The solution (50 µL, 0.5 mM) was applied on a G-25 Quick Spin Column (Roche Diagnostics Corp., IN) to remove $PPG_{400}$, $PPG_{400}$-maleimide adduct, TCEP, and buffer salts, and the DNA-bis ($PPG_{400}$) eluted.

γ-Cyclodextrin 4-thiobutyroxylate. γ-Cyclodextrin (γ-CD, Cerestar Inc.; MW=1297, 500 mg, 0.4 mmol) was dissolved in borate buffer ($Na_2B_4O_7 \cdot 10H_2O$, 3 mL 25 mM aqueous) to yield 133 mM γ-CD, and the pH adjusted to 11.0 with 5% aqueous NaOH solution. Then 2-iminothiolane (Traut's reagent; MB; MW=137.6; 44 mg, 320 µmol) was added to the solution, reducing the pH immediately to 8.5. It was adjusted to 10.0 by addition of more NaOH solution and stirred for 5 hrs. A 150 μL-aliquot of this solution was diluted with borate buffer (3 mL, 25 mM), yielding 6.5 mM thiobutyroxylate γ-CD (γ-CD-SH) and applied on a Sephadex G-10 PD-10 column (bed volume ~2.5 mL, packed in the laboratory). The void volume was discarded, and 3.5 mL of ~5 mM γ-CD-SH was eluted. MALDI-TOF analysis of the solution revealed a composition of 25% γ-CD-SH and 75% unreacted γ-CD). To protect the thiol group, methyl methanethiosulfonate (MMTS, MB; MW=126.2; 10 mg, 70 μmmol 20 mM) was added to this solution and the mixture stirred for 2 hrs. The resulting disulfide (γ-CD-S—S—$CH_3$) was again purified by the G-10 gravity gel filtration column and stored at −25° C.

Rotaxane formation. Aqueous γ-CD-S—S—$CH_3$ (10 μL, 5 mM, 50 nmol) was mixed with DNA-bis($PPG_{400}$) (50 μL, 500 μM, 25 nmol) and held in a vortex mixer for 10 min. The rotaxane solution was stored at −25° C.

Surface tethering. A mica chip was prepared for use as an atomic force microscopy substrate by exposure to aminopropyltriethoxysilane (APTES) vapor for 1 hr, followed by immersion in glutaraldehyde for 5–10 min, following the procedure of Wang et al, *Biophysical Journal*, 2002, 83, 3619, incorporated herein by reference. The previously prepared rotaxane solution was diluted to ~1 μM with $H_2O$, coated dropwise onto the substrate, the terminal amino groups allowed to react with the exposed glutraldehyde for 10 min, and the excess rinsed off with distilled water. TCEP buffer (1 mM; $NaH_2PO_4$, 5 mM; adjusted to pH 7.0 with NaOH) was deposited dropwise on the chip to cleave the disulfide on the cyclodextrin, and AFM studies performed immediately.

AFM spectroscopy. The chip bearing rotaxanes covalently tethered to the surface at both ends was placed in the holder of an AFM (PicoSPM, Molecular Imaging). Areas of the mica substrate were imaged to find locations bearing rotaxanes using MAC-mode™ AFM and a magnetically coated Nanosensor® tip, force constant=2 N/m. Then the tip was changed to a ~0.35 N/m (nominal force constant), and force-distance curves (FDCs) obtained. Tips were calibrated using a Nanodevice® tip by the slope-comparison method of Hinterdorfer et al, Proceedings of the National Academy of Sciences of the United States of America, 1996, 93, 3477, incorporated herein by reference.

FDCs that were obtained fell into two categories: blanks, in which no force was recorded other than that of the tip pressing on and pulling off the substrate; and samples, in which a large change in force was observed after a certain distance. Histograms were plotted from the 56 such curves obtained, and the mean force calculated as 1.01±0.29 nN. This force, too large to be any single event other than covalent bond breaking, is presumed to be the rupture force of the Au—S bond between the tip and the thiol function of the cyclodextrin by comparison with the 1.4±0.3 nN forces required to rupture the bond to thiol-functionalized polysaccharides reported by Grandbois et al, *Science*, 1999, 283, 1727, incorporated herein by reference. The maximum length traversed by the tip upon withdrawal from the surface was found to be 17 nm, or 170 Å. Subtracting 27 and 5 Å for the $PPG_{400}$ and maleimide linker, respectively, results in a distance of 138 Å due only to the DNA. The calculated length of the tethered molecule if it were helical, double-stranded is 50 nucleotides×3.4 Å/nucleotide=170 Å. When the CD has pulled the center of the molecule as far as possible, to form an isosceles triangle with the surface, the maximum distance of 85 Å would be reached, assuming that the two ends are tethered next to each other so that the slope of the molecule is not far from perpendicular. The experimental length is thus 138/85=62% longer than the theoretical length of double-stranded helical DNA. However, stretching of DNA results in extensions of up to 114%, reported by Bensimon, et al, *Physical Review Letters*, 1995, 74, 4754, incorporated herein by reference. The conclusion, therefore is that the cyclodextrin has been slid along the DNA by the AFM tip.

The invention claimed is:

1. A device for sequencing at least a fragment of a linear polymer; said device comprising a location for placement of a rotaxane comprising the combination of at least one cyclic molecule and a linear polymer threaded through said cyclic molecule; a probe attached to the cyclic molecule or the linear polymer that moves the cyclic molecule relative to the linear polymer when the device is in use to produce a signal resulting from the interaction of the cyclic molecule and a unit of the polymer; and means for reading said signal.

2. The device of claim 1 including means to attach the probe to the cyclic molecule or the linear polymer.

3. The device of claim 2 where said means comprises ionic or covalent bonding.

4. The device of claim 1 were the means for reading said signal comprise a member selected from the group consisting of potentiometer for reading redox potentials, a potentiostat for reading current levels, a transducer for reading mechanical deflection, and a spectrophotometric sensor for detecting electromagnetic absorption or emission.

5. The device of claim 1 where the probe is the tip of a scanning probe microscope that moves the probe when the device is in use.

6. The device of claim 1 including means to correlate the signal by comparing the same to a standard with a data base of known signals for previously identified polymeric units.

7. The device of claim 1 including means to tether the linear polymer or cyclic molecule to a surface.

8. The device of claim 1 including means to stretch the linear polymer.

9. The device of claim 1 where the probe is attached to the cyclic molecule.

10. The device of claim 1 where the polymer is a member selected from the group of a nucleic acid, a protein, a non-biological polymer.

11. The device of claim 1 where the cyclic molecule is a member selected from the group of a cyclodextrin, a circular DNA, a calixarene, a crown ether, a cyclic peptide, a .beta.-barrel, cucurbituril, hemolysin, or a metallic nanoring.

12. A process for sequencing at least a fragment of a linear polymer, said process comprising the steps of forming a rotaxane of a linear polymer to be sequenced threaded through a cyclic molecule; attaching a probe to either said cyclic molecule or linear polymer; moving said probe to move said cyclic molecule relative to said linear polymer to produce a signal; and recording said signal.

13. The process of claim 12 where the probe is attached to either of said molecules by an ionic or covalent bond.

14. The process of claim 12 where the probe is attached to the cyclic molecule.

15. The process of claim 14 where the linear polymer is tethered and stretched while said cyclic molecule is moved relative to the polymer.

16. The process of claim 12 where the signal generated is an electrical or mechanical signal.

17. The process of claim 12 including the step of correlating the signal by comparing the same to a standard with a data base of known signals for previously identified polymeric units.

18. The process of claim 12 where the polymer is a member selected from the group consisting of a nucleic acid, a protein, or a non-biological polymer.

19. The process of claim 15 where the polymer is a nucleic acid.

20. The process of claim 12 where the cyclic molecule is a member selected from the group consisting of a cyclodextrin, a circular DNA, a calixarene, a crown ether, a cyclic peptide, a .beta.-barrel, cucurbituril, hemolysin, or a metallic nanoring.

* * * * *